United States Patent [19]

Sjödin

[11] 4,301,373
[45] Nov. 17, 1981

[54] SCANNING OF WORKPIECES SUCH AS LUMBER CANTS

[75] Inventor: Bo Sjödin, Jonköping, Sweden

[73] Assignee: Saab-Scania AB, Linköping, Sweden

[21] Appl. No.: 55,045

[22] Filed: Jul. 5, 1979

[30] Foreign Application Priority Data

Jul. 10, 1978 [SE] Sweden .................................. 7807659

[51] Int. Cl.$^3$ .......................................... G01N 21/30
[52] U.S. Cl. .......................................... 250/560; 250/561
[58] Field of Search .................... 250/560, 561; 356/1; 144/312

[56] References Cited

U.S. PATENT DOCUMENTS

| | | | |
|---|---|---|---|
| 3,890,509 | 6/1975 | Maxey | 250/561 |
| 3,963,938 | 6/1976 | Sanglert | 250/561 |
| 3,983,403 | 9/1976 | Dahlstrom et al. | 250/560 |
| 4,186,310 | 1/1980 | Maxey | 250/561 |
| 4,201,475 | 5/1980 | Bodlaj | 356/1 X |
| 4,227,813 | 10/1980 | Pirlet | 356/1 X |

*Primary Examiner*—David C. Nelms
*Assistant Examiner*—Darwin R. Hostetter
*Attorney, Agent, or Firm*—James E. Nilles; James R. Custin

[57] ABSTRACT

An array camera used to scan elongated workpieces moving through a measuring zone transversely to their lengths has its photoresponsive detector elements aligned lengthwise of the workpieces, with optical axes of the elements lying in a common plane intersecting the measuring zone. Each element "sees" only a small (e.g., 8×8 mm) pixel. Radiation sources are located at opposite sides of said plane and emit radiation towards the measuring zone to be reflected to the elements from workpieces. During each of a succession of short measuring cycles (e.g., 4 millisecond duration) each element is exposed successively to radiation originating from each radiation source to the exclusion of the other, to thus produce an A output and a B output during each cycle, and is also exposed to substantially low level radiation to produce an R output. For each cycle, the R output of at least certain elements is subtracted from the A and the B outputs of the same elements for the same cycle, to produce ΔA and ΔB difference signals. Timing is such that ΔA and ΔB signals for the same element and cycle originate from one and the same small surface area on the workpiece, and therefore inclination of that surface area is ascertainable as a function of the ΔA and ΔB values. During a fourth interval in each cycle, certain elements detect radiation from a laser that has its beam in said plane and oblique to the workpiece surface, and such elements then produce an L output. From the particular elements that produce L outputs, local thickness of the workpiece is ascertainable.

20 Claims, 14 Drawing Figures

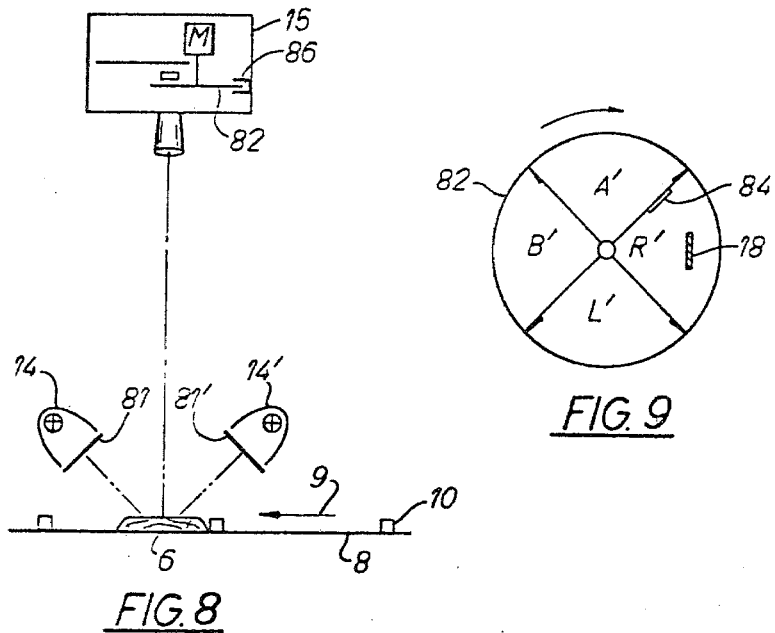
FIG. 8
FIG. 9
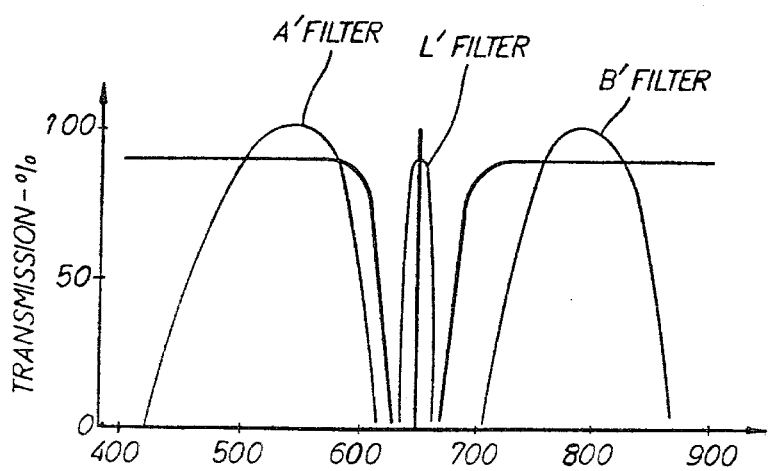
FIG. 10

SCANNING OF WORKPIECES SUCH AS LUMBER CANTS

FIELD OF THE INVENTION

This invention relates to a method and apparatus for automatically taking measurements of the surface characteristics of a workpiece, as for the purpose of determining the trimming that will convert the workpiece to a finished piece of optimum size; and the invention is more particularly concerned with the production of signals which denote surface characteristics of a workpiece that relate to both its geometry and its quality and which can be utilized by a computer for calculation of an optimum reconfiguration of the workpiece.

BACKGROUND OF THE PRIOR ART

U.S. Pat. No. 3,886,372 to B. Sanglert and U.S. Pat. No. 3,983,403 to C. Dahlström et al exemplify the methods and apparatus to which the present invention generally relates. In such methods and apparatus, photoresponsive devices are employed to scan a workpiece and produce signals that can be fed to a computer to enable it to make an evaluation of geometrical features of the workpiece.

A typical workpiece to be scanned with such apparatus is a cant or similar unfinished lumber piece having at least one surface that has been sawed to flatness and having at least one wane surface which is oblique to the sawed surface and which is to be trimmed away in a finishing operation. The information obtained from scanning is employed for calculation of trimming cuts that will convert the particular workpiece into a finished piece of lumber having the highest obtainable economic value, taking into account both market conditions and the configuration of the unfinished workpiece itself. The optimizing calculations can be performed by known data processing equipment, programmed in a known manner, but the accuracy of the results obtained with such equipment is necessarily dependent upon the sufficiency and the accuracy of the data fed into it.

In the prior systems for the automatic measurement of cants and similar unfinished lumber workpieces, as in the system of this invention, an aligned array of photosensitive detector elements scans along elongated zones on the workpiece, which zones extend transversely to the direction in which the detector elements are aligned. Scanning is effected by relative movement between the detector array and the workpiece, produced in any suitable manner. Thus the Dahlström et al patent discloses that the array can be moved while the workpiece is held stationary, or that the workpiece can be moved past a stationary array; and the Sanglert patent discloses that a swinging or rotating mirror can be interposed in the light path between the workpiece and the array to cause successive parts of a stationary workpiece to be imaged onto a stationary array as the mirror swings. Moving the array is unsatisfactory for rapid scanning because of its bulk and the cable connections to it, and the use of a swinging mirror introduces mechanical complexity and increases the changes for measurement errors. On the other hand, prior systems in which the workpiece moved during scanning tended to be slow and inaccurate.

In whatever manner the workpiece has been scanned, it has heretofore been necessary to so illuminate it that one of its wane or side surfaces was put into relative shadow during one part of the scanning operation and its other wane was shadowed during another part of the scan. In accordance with the teachings of U.S. Pat. No. 3,890,509 to C. W. Maxey, this was done by illuminating the workpiece alternately from each of two light sources that cast light laterally across the top surface of the workpiece at opposite low oblique angles. Thus, with illumination of each light source, the wane or edge that was away from it would be in shadow, and there would be a relatively abrupt drop in magnitude of the output signal from each photoresponsive element as its scan moved onto the shadowed wane or edge.

With prior scanning systems wherein such illumination was employed, the workpiece was either scanned twice—once with illumination from each source—or the lighting was changed when the scan had progressed about halfway across the workpiece. With two scans the workpiece had to be stationary during scanning, and the processing rate tended to be slow, whereas single-scan systems tended to be less accurate.

With both types of prior systems it was possible to produce output signals from the photoresponsive array that defined the location of edges of a workpiece and the edges of its wane surfaces, but no other information was obtainable about the workpiece geometry and configuration. Thus, if a scanned top surface of the workpiece was substantially curved across its width, the scanning outputs did not signify information about such curvature.

In those prior scanning systems wherein the workpiece had to be stationary at the measuring station at which scanning took place, relatively complex mechanism was needed for alternately moving and stopping the workpieces; but, more important, stopping each workpiece at the measuring station markedly slowed the flow of workpieces along the processing line, and accelerations of workpieces as they were moved out of the measuring station could cause their orientations to shift so that the measurement data become inaccurate or meaningless.

In prior systems it was considered necessary that the light or invisible radiation used for scanning have a substantially constant level and be of relatively high intensity so that reflection from the sawed top surface of the workpiece would contrast strongly with that from a shadowed wane surface, to ensure a sufficient change in output signal level for accurate identification of the boundary edge between those surfaces. Since prior systems required a perceptible alternation in the operation of the two light sources, the use of constantly changing visible light at a high intensity level was fatiguing to persons who had to work in the vicinity. Of course high intensity illumination also has the disadvantage of high energy consumption.

In such systems as those of U.S. Pat. Nos. 3,983,403 and 3,963,938, measurement errors could arise because different detector elements of an array camera respectively scanned the wane surfaces and the sawed top surface of a cant. It often happens that individual elements in an array have response characteristics which are not accurately matched to the response characteristics of the other elements, with the result that such individual elements produce outputs that are inconsistent with those from the other elements. It can also happen that amplifier drift can affect the outputs of one or several detector elements. Such output signal inconsistencies and distortions will of course affect the accuracy of the measurements made with the scanning system unless compensation is made for them, and heretofore it has not been known how to effect suitable compensation.

SUMMARY OF THE INVENTION

The general object of the present invention is to provide a method and means for employing a linear array of photoresponsive detector elements to scan a workpiece, whereby the output signals from the several detector elements are of such character that they can be utilized in an accurate calculation of profiles or surface contours of the workpiece, notwithstanding that scanning takes place at remarkably high speed and while the workpiece is in the course of steady movement through a measuring zone at which the scanning occurs.

Another general object of the invention is to provide a method and means for scanning a workpiece with the employment of an array of photoresponsive detector elements in order to obtain information for a calculation of the type just described, whereby the radiation needed for illuminating the workpiece for scanning can have a relatively low level of intensity and can be steady, or can appear to be steady, and whereby very accurate measurement data are obtained from the several detector elements, notwithstanding possible amplifier drift and differences in response characteristics as between individual elements.

Another and more specific object of the invention is to provide a workpiece scanning system of the character described whereby complete information can be obtained about the contour of the scanned surface or surfaces of the workpiece, including not only information about the location of edges of the sawed and wane surfaces of the workpiece but also about the amount and kind of curvature that the scanned surface may have.

A further specific object of the invention is to provide a scanning system of the character described that not only scans a workpiece much more quickly than heretofore but has the further important advantage of producing a greater quantity of more accurate data about the workpiece, which data can be employed for a complete determination of the geometrical parameters of the workpiece and can also be employed for evaluation of the quality of every part of it with respect to such defects as knots, holes, cracks and the like.

Another object of the invention to provide a measurement system of the character described wherein compensation is automatically made for nonuniformity of the response characteristics of the individual detector elements of an array camera with which workpieces are scanned, such compensation being effective to compensate for response peculiarities of individual detector elements and also to compensate for such external influences as amplifier drift.

Another specific object of the invention is to provide a scanning system whereby information can be obtained about variations in the thickness of a workpiece along each of a number of strip-like zones that extend across its width.

The objects of the invention are achieved with a scanning system comprising an array that cooperates with optical means and comprises a plurality of adjacent photoresponsive detector elements which have respective optical axes lying in a common plane. Each of said detector elements has a response field that is limited to small angles of divergence from its optical axis, and it produces an output having a magnitude which is related to the intensity of radiation that it detects in its response field. The array is caused to scan a workpiece in a direction normal to said plane and containing said optical axes, at a predetermined velocity, while a pair of radiation sources that are spaced to opposite sides of said plane emit radiation towards the workpiece to be reflected from it for detection by detector elements of the array. According to the invention, a cycle signal is issued at each of a succession of regular and substantially short time periods during scanning of a workpiece, and each pair of successive cycle signals defines a measurement cycle during which the scan is advanced a small distance in said direction. During each measurement cycle, each detector element that has the workpiece within its response field is exposed to radiation that originates from each in turn of said radiation sources substantially to the exclusion of radiation originating from the other, so that the detector element produces during each measurement cycle a pair of discrete measurement output signals, each corresponding in magnitude to the intensity of detected radiation originating from one of said sources. The sequence of said measurement output signals and the interval of exposure to radiation originating from each source is the same for every measurement cycle. Further, the frequency of the cycle signals and the timing of said intervals are so controlled in relation to said predetermined velocity of scan that there is a substantial overlap between the respective areas of the workpiece that are within the response field of an element during said intervals in each measurement cycle, which overlap defines a local area on the workpiece; and the local areas for successive measurement cycles are in proximity to one another. In saying that local areas are in proximity to one another, it is meant that they are not spaced apart by more than a small distance and may overlap one another.

It will be seen that, in contradistinction to prior scanning systems wherein radiation originating from different sources was reflected to a detector element from different areas of a workpiece, the system of the present invention is characterized in that a detector element by which a workpiece is scanned is, during the course of a brief time interval, exposed to radiation which is reflected to that element from substantially one and the same small surface area on the workpiece but which originates first from one and then from the other of two radiation sources that are spaced to opposite sides of the optical axis of the detector element.

In one mode of practicing the invention, the radiation sources are energized alternately, to cause each detector element, during each of said intervals of exposure, to detect radiation from one radiation source to the exclusion of that from the other. In an alternative mode, each of said radiation sources is caused to steadily emit radiation of a wavelength substantially different from that emitted by the other, and filters are alternately passed in front of the detector element that respectively block radiation of one and the other of said wavelengths.

In a preferred mode of practicing the invention, each measurement cycle has a further interval during which each detector element in the array is subjected to a reference level of radiation intensity, substantially below the intensity level of detected radiation originating from said sources, to cause the detector element to produce a reference magnitude output. The reference magnitude issued by each element during each measurement cycle is subtracted from the magnitude of each of the measurement output signals issued by the same element during the same measurement cycle, to produce difference signals that are directly comparable with one another and with difference signals originating from other elements, irrespective of the response characteristics of the particular elements.

The invention also contemplates production of thickness signals which contain information about variations in a thickness dimension of a workpiece across another dimension of it. Said thickness signals are produced during a further interval in each measurement cycle by causing a narrow beam of radiation of be emitted—as from a laser—substantially in the plane of the optical axes of the detector elements and at an oblique angle to a surface of the workpiece towards which the beam is emitted, so that reflection of said beam from said surface produces a spot of radiation which can be detected by said detector elements, and which causes a thickness signal to be produced by an element that detects it. A function of local workpiece thickness is thus given by the identity of the particular element that produces the thickness signal.

Other features of preferred modes of practicing the invention are set forth in the detailed description hereinbelow.

BRIEF DESCRIPTION OF THE DRAWINGS

In the accompanying drawings which illustrate the modes of embodying and practicing the invention that are now regarded as preferred:

FIG. 6 is a composite diagram illustrating the illumination and scanning of a workpiece as it passes through the measuring zone, together with the signals issued from an individual detector element at successive stages of their scan and one mode of processing the signals, wherein FIG. 6a depicts a typical workpiece, shown in end view, in its relation to the array camera and to radiation falling upon it at one instant during scanning; FIG. 6b shows a segment of the workpiece as seen from above and depicts the several incremental areas on the workpiece that are scanned by one detector element during successive measurement cycles through the time of scanning; FIG. 6c diagrammatically depicts several difference signals obtained in the course of scanning across the workpiece for each interval in which the workpiece is illuminated from the front; FIG. 6d is a diagram similar to FIG. 6c, but for intervals during which the workpiece is illuminated from the rear; and FIGS. 6e and 6f illustrate the integrated difference signals of FIGS. 6c and 6d, respectively;

FIG. 8 diagrammatically illustrates a modified form of apparatus for practicing the invention with steady radiation from the radiation sources;

FIG. 9 illustrates a filter disc for the apparatus of FIG. 8;

FIG. 10 depicts the wavelengths of the several radiation sources employed with the FIG. 8 apparatus and filtration of those radiations by the FIG. 9 disc;

DETAILED DESCRIPTION OF PREFERRED EMBODIMENT OF THE INVENTION

Figure 1:
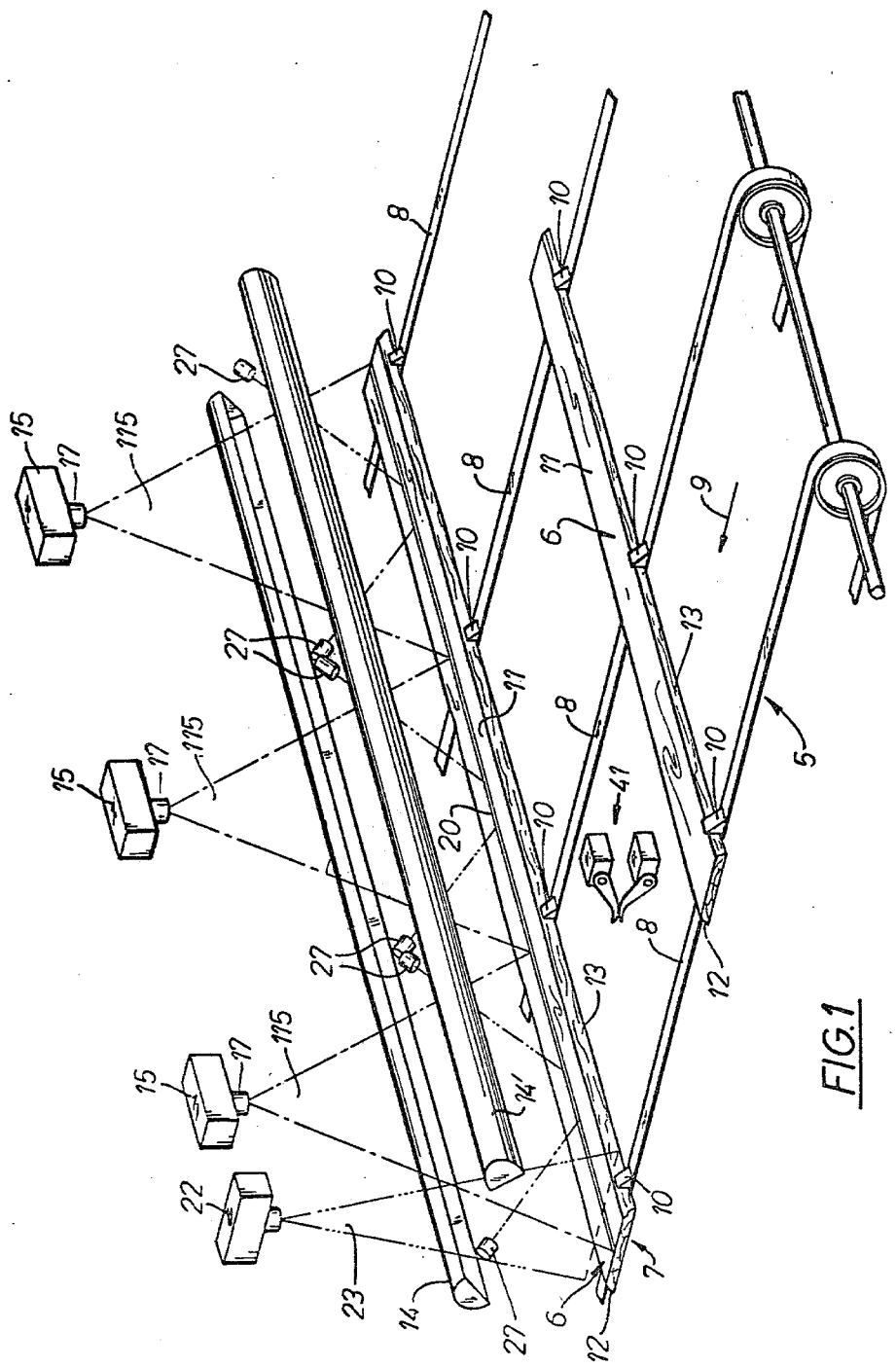
FIG. 1 is a more or less diagrammatic perspective view of apparatus embodying the principles of the present invention.
Figure 2:
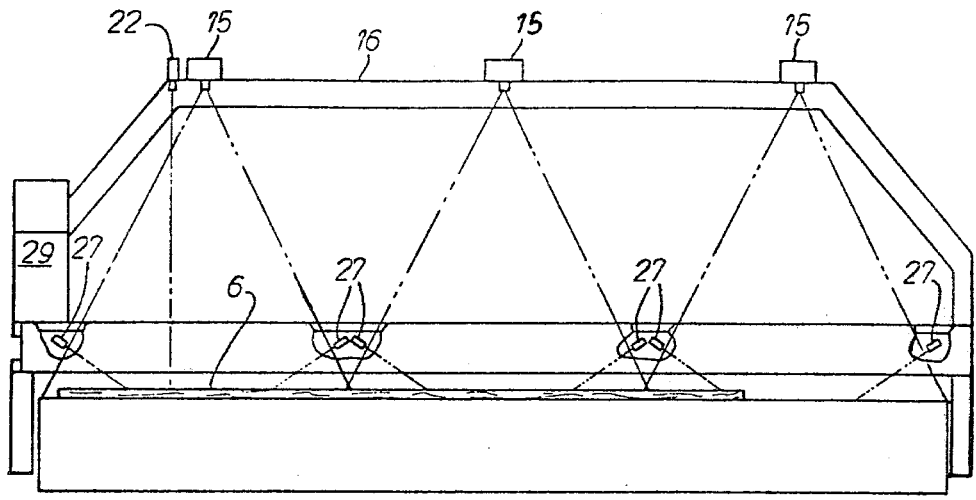
FIG. 2 is a view of the part of the apparatus that is at the measuring zone, as seen in end elevation.

Referring now to the accompanying drawings, the numeral 5 designates generally a conveyor by which workpieces 6 that are here illustrated as lumber cants are transported through a measuring zone 7 at which scanning of each workpiece takes place in accordance with the principles of this invention. The conveyor 5 can be of any suitable type and is here illustrated as comprising endless drive members 8 such as belts or chains, arranged to have parallel upper stretches extending in the direction of transport of the workpieces 6, which direction is designated by the arrow 9.

Each of the workpieces 6 rests on two or more of the endless drive members 8 and extends transversely to their upper stretches so that the workpieces move transversely to their own lengths. For the purposes of the invention it is necessary that there be some space between adjacent workpieces, but the distance between successive workpieces need not be substantially greater than about 200 mm. Notwithstanding the need for such spacing, a high rate of processing is possible (typically, 60 workpieces per minute) because with the present invention the workpieces can move at a steady and rather fast rate (e.g., 1.2 m/sec.) both while in the measuring zone 7 and while traveling to and from it.

To ensure that the workpieces 6 partake of all motion of the conveyor 5 and maintain their respective orientations on it, and to facilitate proper spacing of the workpieces along the conveyor, dogs 10 can be affixed to the drive members 8 at substantially uniform lengthwise intervals. If the workpieces 6 are lumber cants, they will normally be placed on the conveyor 5 with their narrower sawed surfaces 11 uppermost, which is to say that their wane surfaces 12, 13 face obliquely upward.

In the measuring zone 7 the workpieces are illuminated from radiation sources 14, 14', as described hereinafter, and are scanned by one or more so-called array cameras 15. The radiation sources 14, 14' and the array cameras 15 are stationarily supported above the conveyor 5 on a frame 16 that bridges across the conveyor at the measuring zone.

Each array camera 15 is of a known type that comprises a wide angle lens 17 by which the image of the workpiece 6 in the measuring zone 7 is brought to a focus at a row of photorespective detector elements 18 in the camera. A typical such camera has photodiodes as its detector elements, in an array functionally equivalent to a line of 1024 individual photoelectric cells. The lens 17 cooperates with each detector element to define for it an optical axis and to restrict its response field to within small angles of divergence from its optical axis, so that the element "sees" only a relatively small area 19 of the surface of a workpiece in the measuring zone. That small area 19 or so-called pixel, at the workpiece, is typically about 8 by 8 mm., including optical distortion. All of the elements of the array have their optical axes in a common plane 115.

The detector elements 18 of each array camera 15 are aligned transversely to the direction 9 of conveyor movement—that is, lengthwise of a workpiece 6 in the measuring zone 7—so that as a workpiece moves through the measuring zone, each detector element scans it along a narrow strip 20 that extends across its width. Since there are only relatively small distances between the strips 20 scanned by adjacent detector elements, to afford high measurement precision, two or more array cameras 15 will usually be mounted side by side with their response fields endwise contiguous to one another, to accommodate long workpieces. Thus, as shown in FIG. 1, three array cameras 15 are employed to scan workpieces up to 24 feet long.

The magnitude of the electrical output from a detector element 18 corresponds to the product of the intensity and the duration of radiation to which that element is exposed. With the present invention, exposure intervals are brief and of uniform duration; hence for any such interval, the magnitude of the output of a detector element depends upon the intensity of radiation reflected to it from the workpiece surface pixel 19 that is then within its response field.

Figure 3:
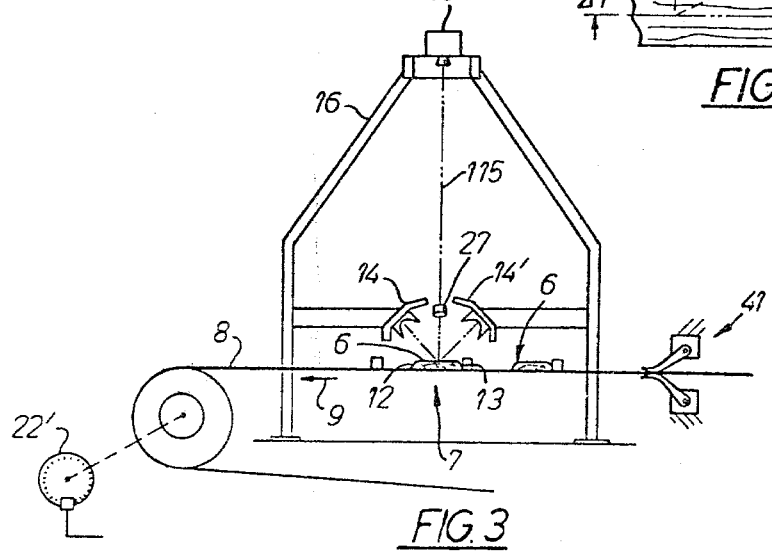
FIG. 3 is a view of the measuring zone apparatus in side elevation and in a slightly modified form.

As will appear more fully as the description proceeds, it is necessary that the output signal from each detector element at any instant shall be related to the then-existing position of the workpiece 6, which is to say that there must be information corresponding to the position across the width of the workpiece of the pixel 19 from which each element is detecting reflected radiation. For that purpose a position pulse signal is issued for each uniform increment of motion of the workpiece through the measuring zone 7. The position signals can be produced by means of a photo-mechanical pulse emitter 22' (see FIG. 3) comprising a slotted disc coupled for rotation to an endless drive member 8 of the conveyor, a light source on one side of the disc, and a photodiode at its other side that issues an electric pulse each time the conveyor moves through a predetermined distance. Alternatively, as shown in FIG. 1, a further array camera 22 can be employed to issue position signals. The position array camera 22 is generally like the array cameras 15 but has its detector elements aligned in the direction 9 of conveyor motion so that its response field 23 extends across the measuring zone, and it issues position information as the workpiece moves across the response fields of its several detector elements.

Each of the radiation sources 14, 14' that illuminates measuring zone 7 can comprise a gas discharge tube in cooperation with a parabolic reflector. Because the radiation sources 14, 14' may produce either visible or invisible light, the general term "radiation" is herein used for their output. The two radiation sources 14 and 14' are spaced above the measuring zone 7 and to opposite sides of the plane 115 that contains the optical axes of the array camera detector elements, so that each casts its radiation at an oblique angle (e.g., 45° to the horizontal), transversely across the width of a workpiece in that zone. It will be seen that for the purposes of the invention the angles at which radiation is emitted from the sources 14, 14' need not be low ones in relation to a workpiece, and in fact, contrary to past practice in this art, it is preferred that the radiation sources be high enough so that ordinarily each wane surface 12, 13 on a cant will be illuminated by both radiation sources 14, 14'.

In one mode of practicing the present invention, apparatus that is described hereinafter causes the radiation sources 14, 14' to be illuminated alternately at a relatively high frequency of alternation. In another mode, more fully explained hereinafter, radiations of different wavelengths are steadily propagated from the respective sources 14 and 14', and a filter disc associated with the optical systems of the array cameras 15 alternately filters out radiation of each of those wavelengths.

Figure 7:
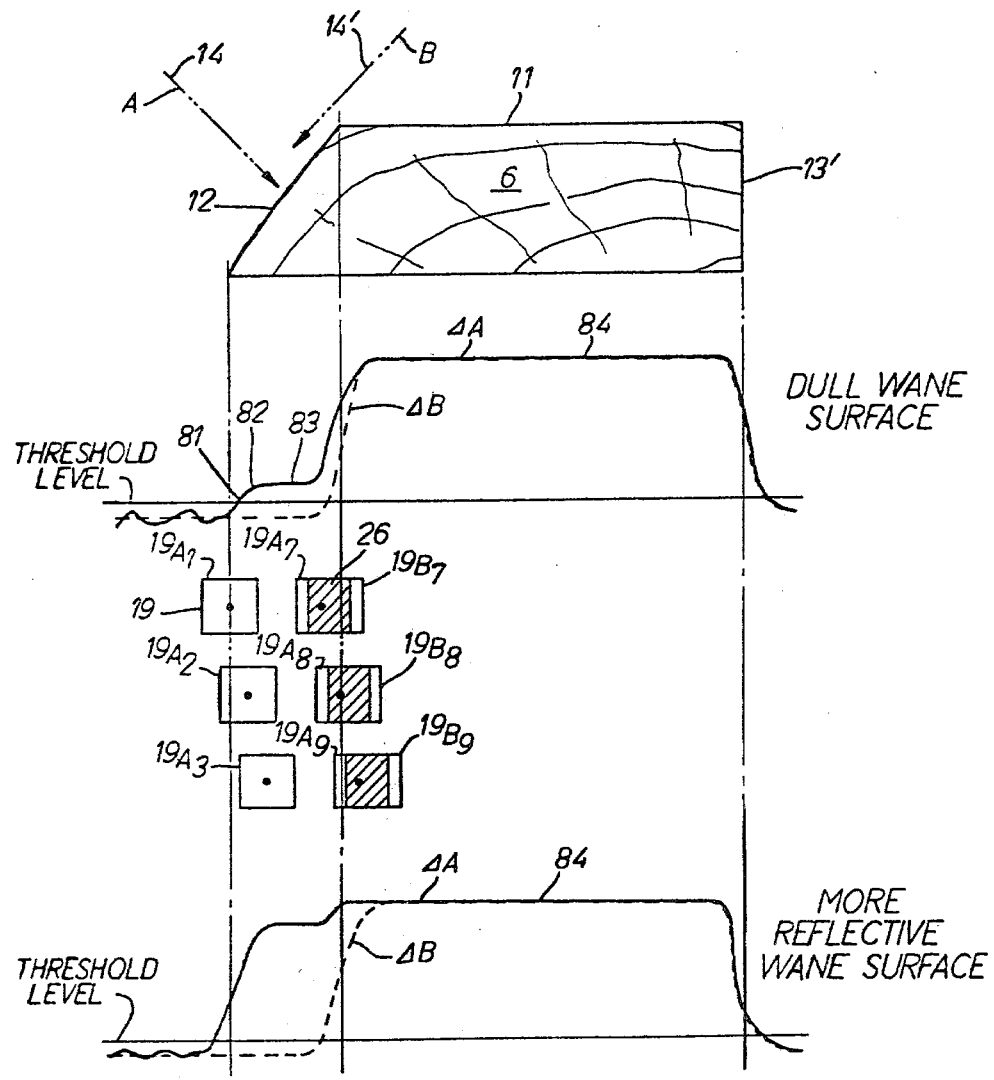
FIG. 7 is a composite diagram showing the relationship of pixels scanned by a particular detector element in successive measurement cycles and the signals resulting from scanning according to another and preferred mode of practicing the invention.

In either case, as each detector element 18 detects radiation reflected from a workpiece, its output takes the form of a series of short pulses, comprising an A pulse for each brief interval in which the element is exposed to radiation originating from the front radiation source 14 and a B pulse for each interval in which it is exposed to radiation originating from the rear radiation source 14'. Each such interval of exposure can be about one millisecond. The A pulses and B pulses are produced in a regular sequence. Cycle signals are also produced at regular intervals such that two successive cycle signals define a measurement cycle during which at least one A pulse and at least one B pulse are produced. The sequence of A and B pulses is the same from measurement cycle to measurement cycle, and measurement cycles are of course simultaneous and alike for all array cameras as well as for all detector elements of an array. The sequence and duration of the exposures that give rise to the A and B pulses are so controlled in relation to the speed of movement of a workpiece through the measuring zone that the pixel 19 on a workpiece for any one detector element during an A pulse interval of a measurement cycle has a substantial overlap with the pixel for that same element during the B pulse interval of the same measurement cycle. The area of such overlap, designated 26 in FIG. 7, is herein termed a local area.

From a method aspect, therefore, the invention contemplates an iterative measurement cycle, repeated many times as each workpiece passes through the measuring zone, and during each measuring cycle at least one A pulse and one B pulse are issued from each detector element that has the workpiece in its response field, each such pulse output being produced in response to radiation reflected from one and the same local surface area 26 of the workpiece, but under illumination of that local area that originates alternately from the two radiation sources 14 and 14'. The sequence of different exposures is uniform for all measurement cycles, and the duration of the measurement cycles, which is determined by the intervals between successive cycle signals, is likewise uniform.

In the preferred practice of the invention, each measurement cycle includes—in addition to at least one A signal and at least one B signal—at least one signal that is obtained by exposing the detector element to radiation of a substantially lower intensity than that which gives rise to the A and B signals. That third type of signal, which is used for reference level purposes as explained below, is herein designated an R signal. It preferably has the same duration (about 1 millisecond) as each of the A and B signals.

The R signal level of radiation intensity—which can be zero radiation—can be produced in any of several ways. For example, both of the radiation sources 14, 14' can be turned off during each interval when the R signal is to exist, so that the R signal is a function of the ambient lighting; or both of the radiation sources 14, 14' can be operated at a substantially reduced level of intensity during the R signal interval; or in the alternative mode involving a rotating filter disc, that disc can include a screen segment whereby radiation is blocked from all detector elements. In any case, the radiation level to which the detector elements are exposed during the R signal interval is preferably uniform for all detector elements and for all measurement cycles.

Figure 4:
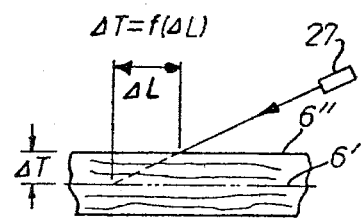
FIG. 4 is a diagram explaining how thickness measurements are made with laser beams according to the invention.
Figure 13:
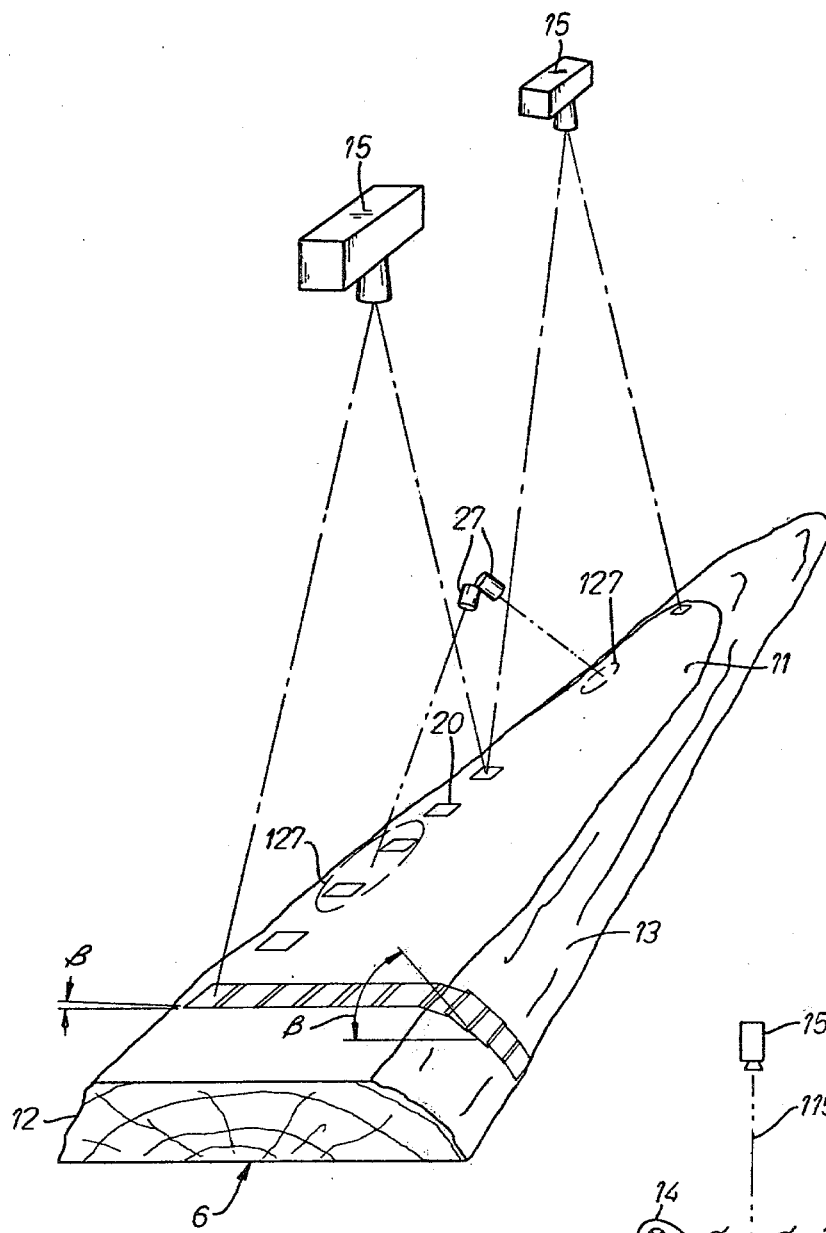
FIG. 13 is a diagrammatic perspective view illustrating the meaning of the angle $\beta$ and depicting certain relationships involved in laser thickness measurement.
Figure 14:
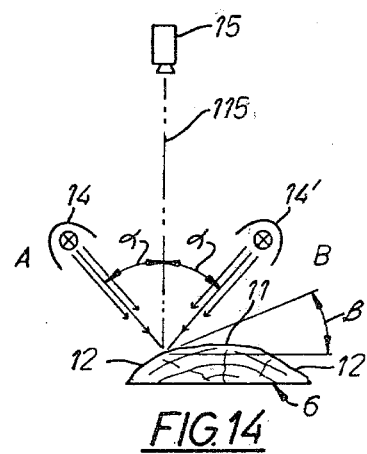
FIG. 14 is a diagrammatic view illustrating the relationships of the angles $\alpha$ and $\beta$ at a local area on the surface of a workpiece which is shown in end view.

For reasons which will appear as the description proceeds, each measurement cycle preferably includes a fourth interval during which certain of the photorespective elements—a relatively small number of them—produce an L signal in response to a spot 127 (see FIG. 13) of laser radiation that appears within their response field during the portion of the measurement cycle allotted to that signal. The radiation which gives rise to the L signals originates from each of a plurality of lasers 27 that are mounted on the frame 16 above the measuring zone, in positions outside the response fields of the array cameras. The narrow beam emitted by each laser 27 lies in the plane 115 of the optical axes of the detector elements in the array cameras 15 and is thus emitted in a direction generally lengthwise of a workpiece 6 in the measuring zone, but it is at a substantially low oblique angle—e.g., 30°—to the horizontal. As can be seen from FIG. 4, there is a relationship between the incremental local thickness ΔT of the workpiece and the projected incremental distance ΔL along the workpiece between the spot of light 127 (see FIG. 13) produced by a laser 27 and the laser that produces it. Thus, on a thin workpiece 6' the spot of light 127 from a given laser 27 is farther from the laser, lengthwise along the workpiece, than on a thick workpiece 6''. Hence, the local thickness of a workpiece can be determined trigonometrically on the basis of the particular detector element that emits an L signal in response to a spot of light produced by a laser. The lasers 27 are preferably so located that their reflection spots 127 are spaced apart at substantially uniform distances along the workpiece, and there are preferably two lasers for each array camera 15.

Preferably each laser 27 is pulsed to emit its radiation only during the interval in each measurement cycle that is alloted to the L signal, which interval can have the same duration (about one millisecond) as the A, B and R signal intervals. The preferred sequence of the several different types of signals during a measurement cycle is one in which an R signal is interposed between each L signal and the directly subsequent A or B signal, as for example R–A–B–L or L–R–A–B. If an A or a B signal directly followed an L signal, the A or B signal from the detector elements that had emitted the L signals might be distorted by remanence due to the high intensity of the laser radiation. It will be understood that more than one R signal may be produced during a measurement cycle, so that a cycle sequence could be A–R–B–R–L–R, for example.

Figure 5:
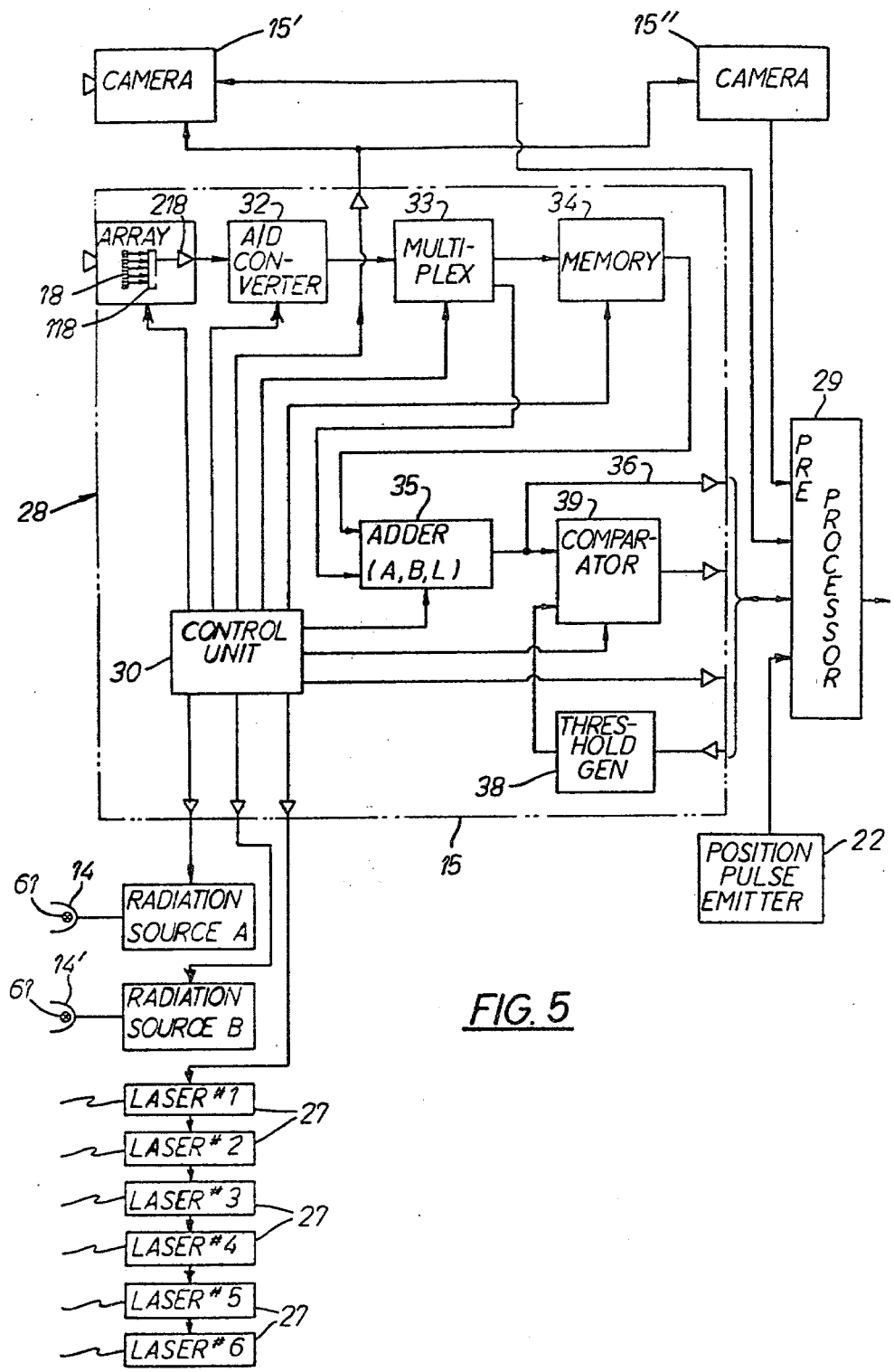
FIG. 5 is a block diagram of signal processing apparatus according to the invention.

Turning now to the signal processing apparatus that is illustrated in FIG. 5, each array camera 15 has certain signal processing equipment 28 associated with it, but only that for one of the array cameras is illustrated in detail. It will be understood that the array cameras 15 and their associated equipment 28 operate in parallel, and they are all connected with a preprocessor 29 which can be mounted on the frame 16 and from which inputs are issued to a computer (not shown) that operates in a known manner to make calculations of the optimum finishing cuts to be made on each workpiece. Each of the array cameras 15 has a control instrumentality 30 associated with it, and one of them can serve as a master unit while the remaining array camera or array cameras 15', 15'' can be slaved to that one.

Within each array camera 15 its photodiode array 18 is coupled in an integrated circuit to a shift register 118 in an arrangement of the type known as a CCD or CCPD. After each exposure, during an interval of no more than a few microseconds, the respective charges on the 1024 photodiodes of the camera are transferred in parallel to the shift register 118 under the control of a clock frequency developed by the control instrumentality 30. The outputs are analog signals, and for the purposes of subsequent processing, they are fed in succession from the camera shift register 118 through an amplifier 218 to an analog/digital converter 32 under control of strobe pulses from the control instrumentality 30 at a frequency on the order of one to ten mHz.

If the output of every one of the 1024 diodes of the array were processed, the flood of information would require a very large memory capacity in the preprocessor 29, but in fact all of that information is not needed for practical measurement purposes. Therefore the strobe pulses are issued to the A/D converter 32 at such frequency that only signals from every nth detector element are processed, as for example every fourth, eight or sixteenth element, so that with a pixel measurement resolution of 2×2 mm., measurements are taken at intervals of 8, 16, or 32 mm along the length of the workpiece. These measurement intervals can be adjusted to suit conditions by providing for adjustment of the strobe pulse frequency. It will be understood that the selection of signals that are to be processed and discarded, respectively, can take place at a subsequent stage of processing, but it is more convenient and efficient to do so at the A/D converter 32.

The digitized signals issuing from the A/D converter 32 are fed to a multiplex 33 which is also controlled from the control unit 30. The multiplex 33 has two outputs, one to a short-term memory 34 and the other to an adder 35. With the above described measurement cycle comprising an R–A–B–L signal sequence, the multiplex 33 feeds to the memory 34 each R signal that issues from the A/D converter 32 and forwards to the adder 35 each in turn of the A, B and L signals issued from the same detector element during the same measurement cycle. At the adder 35, under the control of pulses from the control unit 30, the magnitude of the reference level signal R produced by each nth detector element during each measurement cycle is subtracted from the respective magnitudes of the A, B and L signals for the same detector element and measurement cycle, to produce difference signals ΔA, ΔB and ΔL, respectively, for that detector element and measurement cycle. The "emptying" of the shift register through the A/D converter and the processing of the signals proceeds according to the outputs of elements from one end of the array to the other and goes back to the starting end in a repetitive processing cycle.

All of the ΔA and ΔB signals thus obtained are forwarded by way of a connection 36 to one of the inputs of the preprocessor 29, to be stored in its memory. The ΔL signals are also forwarded to the preprocessor 29 to be stored, but not until after they have been further processed as described hereinafter.

In parallel with the feeding of ΔA, ΔB and ΔL signals to the preprocessor memory, position signals from the position signal emitter 22 are fed to that memory, denoting the relative position of the workpiece, so that coordinate values are known for each group of ΔA, ΔB and ΔL signals originating from a particular detector element during each measurement cycle.

For each position signal, the group of ΔA, ΔB and ΔL values produced at the same time as the position signal is stored. If two or more such groups are produced between successive position signals, the groups produced between position signals are discarded, so that the duration of a measurement cycle can be short and independent of the velocity of workpiece transport.

From one measurement cycle to the next, the workpiece will have advanced a small distance—typically 4 mm.—so that with an 8×8 mm pixel the local area of the workpiece from which a detector element takes information during a particular measurement cycle is in proximity to the local area from which the same element takes information during its next succeeding measurement cycle. "In proximity" here means that such local areas may be overlapping to some extent, or may border upon one another, or may be spaced apart but by no more than a small distance.

At this point it will be observed that at the conclusion of scanning of a workpiece, the preprocessor has stored information which, in its totality, constitutes an electronically readable collection of data relating to points—or, more accurately, local areas—distributed uniformly all across and along the scanned surface of the workpiece. It can be seen that the "tightness" of the matrix or checkerboard of local areas from which information is taken can be readily controlled by selection of the nth detector elements from which signals are processed and/or by taking and processing signals from only every second, or only every third measurement cycle. With increasing "tightness" (smaller and more numerous local areas) there will be a corresponding increase in measurement accuracy, but also a requirement for increased capacity of the preprocessor memory and increased difficulty in processing all of the data within the available time. In practice, it has been found that for taking measurement data at 32 mm. intervals along the length of the workpiece, and with the scan advancing 4 mm per measurement cycle and information taken for every measurement cycle, a 16K-byte preprocessor memory is suitable for storage of the ΔA and ΔB values. Since the short term memory 34 must store for the duration of a measurement cycle an R output from each of the detector elements from which outputs are used, it can be a random access integral circuit memory of suitable capacity.

It will be observed that of the 1024 pixels scanned by an individual array camera during a measurement cycle, only a few, confined to two locations, are illuminated by laser radiation. At each of these locations, however, two or more pixels (usually three, but there may be as many as six) are laser illuminated, owing to the low oblique angle of the laser beam and its consequent divergence at the workpiece surface; and it is therefore necessary to determine the center of the laser beam responsible for each group of L signals. For this purpose, the equipment 28 that is associated with each array camera 15 includes a threshold value generator 38 for producing an output having a magnitude which is above the background value by an arbitrary amount that is preferably adjustable manually. The output of the threshold generator 38 is fed to a comparator 39, which also receives ΔL inputs from the adder. If a ΔL signal has a magnitude greater than that of the threshold generator output, the comparator 39 causes that ΔL signal to be, in effect, accepted and stored in the preprocessor memory; but if the ΔL signal has a magnitude lower than that of the threshold generator output, it is in effect discarded. From the magnitudes of the stored ΔL signals originating from each group of adjacent detector elements, the "center of mass" of that ΔL signal group is calculated, giving the position of the laser beam center at the workpiece surface. This calculation preferably takes place in the preprocessor 29, and the result is fed to a special address in the preprocessor memory. Since a ΔL signal for each laser 27 is generated for each scanning cycle—typically, for each 4 mm. advance of a workpiece—it is readily possible to obtain a series of thickness values extending in a strip across the workpiece at each of several more or less uniformly spaced locations along its length.

Although the stored thickness values contain a substantial amount of data about the profile of the scanned surface of a workpiece, the ΔL signals are related to an arbitrarily defined reference plane, and therefore they do not necessarily define the exact cross-section of the real workpiece, because the bottom surface of the workpiece may be above or below the reference plane, or partly above it and partly below it, as when the workpiece is twisted or warped.

For that reason—unless all workpieces have a known and uniform thickness—the ΔL signal information is preferably supplemented by mechanical thickness measurement, made with a known thickness gaging device 41 comprising a transducer to which upper and lower caliper arms are connected. One or more such devices are mounted ahead of the measuring zone, and each workpiece passes between the caliper arms and diverges them by an amount dependent upon its thickness. The output of each device 41 corresponds only to the maximum thickness of the workpiece in the transversely extending zone at which it is gaged, but it serves for correction or calibration of the laser-derived data.

Returning now to consideration of the ΔA and ΔB difference signals, the use of those signals, rather than of the A and B signals themselves, avoids certain inaccuracies that existed with prior scanning systems (e.g., errors due to drift of amplifier 218) and, in addition, opens new possibilities for obtaining significant information that was not available with prior systems. Thus the ΔA and ΔB difference signals that originate from a particular detector element are inherently compensated for its particular response characteristics, and they are also directly comparable with all other ΔA and ΔB signals, originating from all other elements, irrespective of the particular dynamic response characteristics of the detector elements involved. As a result information is obtainable from the ΔA and ΔB signals that was not available from prior scanning systems.

For workpieces of the type with which the present invention is concerned, the scanned surfaces are diffusing reflectors. Generally, therefore, the intensity of radiation reflected from a pixel on the surface of a workpiece—and consequently the magnitude of the difference signal ΔA or ΔB resulting from exposure to such reflected radiation—is essentially dependent upon the angle of incidence α (see FIG. 6) at which the reflected radiation falls upon the pixel, measured in relation to a perpendicular to the surface area that comprises the pixel.

With the workpiece illuminated from the front light source 14, as shown in FIG. 6a, the angle of incidence $\alpha_1$ for the front wane 12 is small as compared with the angle of incidence $\alpha_2$ of radiation on the sawed horizontal surface 11. Assuming that the surfaces 11 and 12 have like reflectance, the difference signal ΔA that is produced in response to reflection of front oblique radiation from the wane surface 12 will have a larger magnitude than the difference signal ΔA for any portion of the sawed surface 11, owing to the difference between $\alpha_1$ and $\alpha_2$, and for the further reason that a greater area of the front wane surface 12 is within the response field of the detector element, due to the inclination of that wane surface. The lowest ΔA signal magnitude with front oblique radiation will be obtained at the rear wane 13, where the angle of incidence $\alpha_3$ has the highest value.

Under radiation from the rear radiation source 14', the differences in magnitude for the ΔB signals will of course be the reverse of those for the ΔA signals. In practice, the magnitude of a ΔA or ΔB difference signal for an illuminated wane surface such as surface 12 in FIG. 6a will usually be about equal to that for a flat sawed surface like the surface 11, or may be slightly lower, because a wane surface has a lower reflectance than a sawed surface.

However, from the respective magnitudes of the ΔA and ΔB signals for a given local surface area, the angle of inclination β of that local area (see FIG. 13) can be ascertained on the basis of the following relationship:

$$\beta = \arctan\left[-\cot\alpha\, \frac{\Delta A - \Delta B}{\Delta A + \Delta B}\right]$$

This relationship is independent of such external factors as reflectance of the local area and like types of variations in the radiation from sources 14 and 14'.

It will be apparent that if the surface inclination β is determined for each of numerous local areas along a strip 20 across a workpiece that is scanned by a detector element, the profile of the workpiece along that strip will be defined by such data, provided that it is combined with data about the width of the workpiece at that strip and its maximum thickness along that strip. All such information is of course made available in a scanning system operating according to the principles of this invention.

There are various ways of using the ΔA, ΔB and ΔL signals that are obtained with the scanning system of this invention to provide information about workpieces.

One possibility is to employ the ΔA and ΔB difference signals for quality evaluation, that is for detection of the location of defects in a workpiece. However, in the present state of the art it would not be feasible to process the outputs from one scanning operation for both quality evaluation and geometrical measurement, because the amount of data to be processed would probably exceed the capabilities of economically practical equipment.

For quality evaluation, the ΔA and ΔB outputs, produced as explained above, can be compared with a threshold value that corresponds to the value of a ΔA or ΔB signal that would originate from a detector unit if it "saw" a surface area of a particular critical character, such as a wane surface, knot, hole, crack or other surface irregularity that tends to reduce economic value. The threshold value can be selected empirically in accordance with the particular criterion to be used for purposes of the evaluation procedure. Alternatively, the ΔA and ΔB signals can be fed to a memory, corresponding to the memory in the preprocessor 29, and by applying known pattern recognition techniques to the data thus stored, it is possible to identify significant defects in the workpiece and the locations of those defects, as a basis for determining finishing cuts that will convert the workpiece to a finished piece of optimum economic value.

Because the ΔA and ΔB signals can be used to obtain information about local surface inclination β and about surface defects, scanning data obtained in accordance with this invention can be used for measuring surface smoothness, provided that suitably small pixels are chosen for that purpose.

The ΔA and ΔB signals can be employed in various ways for determining the geometry of a workpiece.

Figure 6:
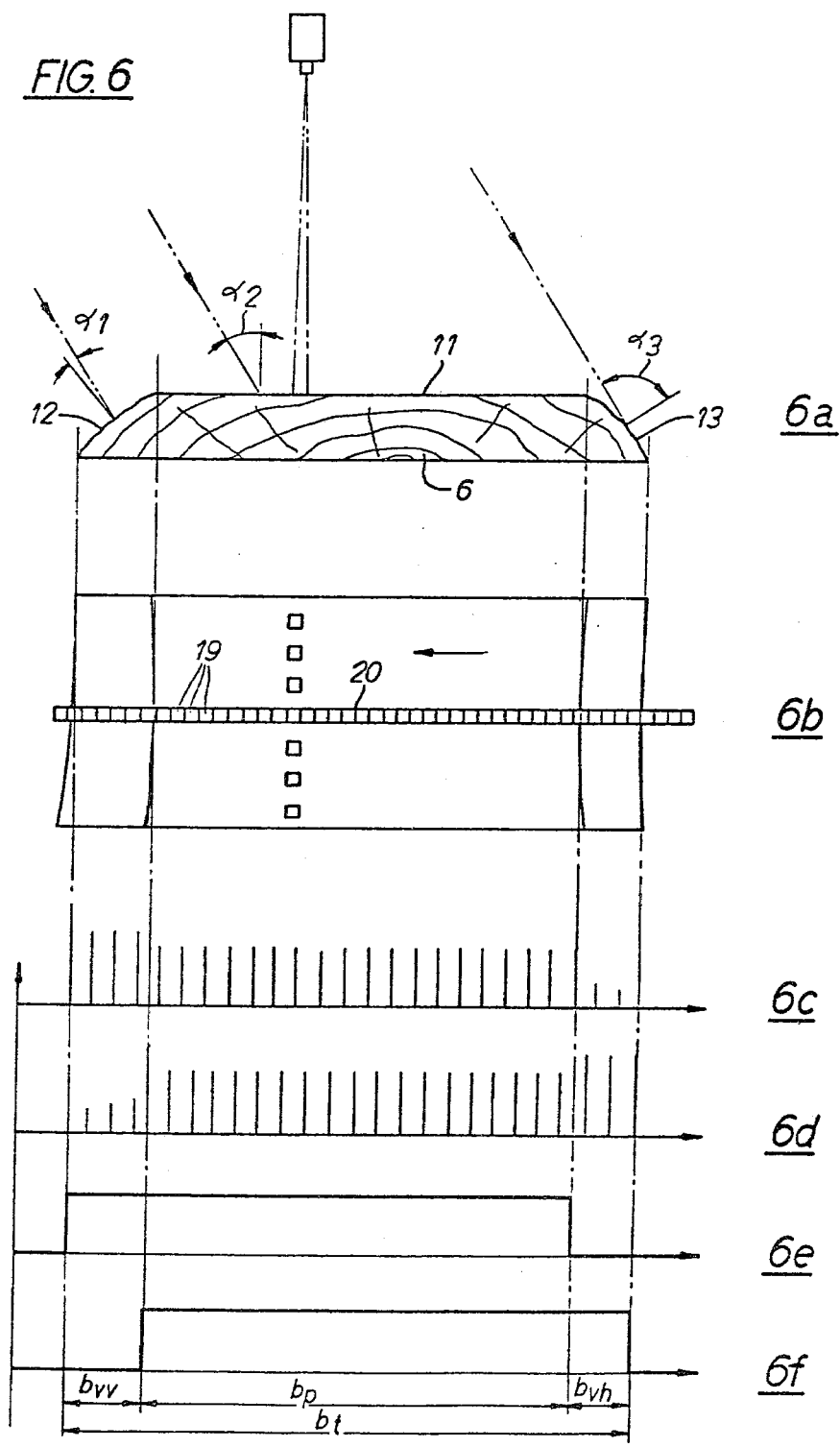

A less accurate and therefore less desirable procedure, but one that may be faster and can perhaps be practiced with less complicated equipment, is illustrated in FIG. 6. FIGS. 6c and 6d respectively depict the ΔA and the ΔB difference signals that are produced by a given detector element as it scans across a lumber cant workpiece, showing the comparative magnitudes of those signals as the scan of the element successively passes the front wane 12, the sawed top surface 11 and the rear wane 13. In reality, since these two sets of signals issue successively from one and the same detector element, the ΔA and ΔB difference signal outputs for that element would appear as a superimposition of FIGS. 6c and 6d. However, the respective ΔA and ΔB difference signals are separated from one another and digitally filtered to produced filtered signals as shown in FIGS. 6e and 6f, respectively. As shown in FIG. 6f, comparing the filtered signals enables a determination to be made of such workpiece magnitudes as the total width $b_t$ of the workpiece, the width $b_p$ of the sawed surface 11, and the width $b_{vv}$ and $b_{vh}$ of the respective wanes 12 and 13. These magnitudes are of course available for each of the narrow strips 20 across the workpiece along which a detector element has made its scan. The digital filtering eliminates disturbing exceptional measurement values that may originate, for example, from splinters and the like, and it also facilitates detection of significant changes in signal magnitude.

Thus, as can be seen from FIG. 6f, an abrupt change in one of the filtered ΔA or ΔB difference signals, from one magnitude that has persisted through several measurement cycles to another magnitude that persists through several measurement cycles, signifies the location of an edge that constitutes a boundary between two surfaces on a workpiece.

The procedure just described is satisfactory for locating edges on a workpiece on which all scanned surfaces are more or less flat, and with an accuracy no better than plus or minus the distance that the workpiece moves during a measurement cycle.

In the preferred and more accurate procedure, by which measurements can be made on scanned surfaces that are not only flat but also on those that are curved, the pixels from which ΔA and ΔB signals originate during one measurement cycle not only substantially overlap one another but preferably also overlap those from which ΔA and ΔB signals originate during the next succeeding measurement cycle. This can be seen from FIG. 7, which depicts the position transversely of a workpiece, in each of a succession of measurement cycles, of the pixels 19 from which ΔA and ΔB signals originate, pixels for successive measurement cycles being denoted by subscripts. With a speed of workpiece transport of 4 mm per measurement cycle and an 8×8 mm pixel area, ΔA signal pixels for successive measurement cycles will overlap one another by 4 mm., as will ΔB signals for successive cycles. The pixel from which a ΔB signal originates during a given measurement cycle will overlap the ΔA pixel for that cycle by about 7 mm.

As a workpiece moves towards the measuring zone, and until its leading edge moves into the pixel for a detector element, the ΔA signal from that detector element will lie below a threshold value which is a little above the background noise level and which is shown in FIG. 7. That threshold value is established by the preprocessor software. During the first measurement cycle in which the workpiece comes within the response field of a detector element, only a part of the pixel for that detector element will be on the workpiece, and for that measurement cycle, therefore, the ΔA signal from that element will be above the background level but, as indicated at 81, it will have a low value, in approximate correspondence with the amount of workpiece surface area that is within the pixel. The same will be true of the ΔB signal if the front wane surface 12 is at such an angle as to reflect radiation from the rear source 14'. For each of the next one or two measurement cycles the ΔA (and ΔB) level will be successively higher, as at 82, reaching a "plateau" 83 when each pixel scanned by the element lies wholly on the front wane surface 12. The value of the ΔA (and ΔB) signals for that "plateau" will depend upon the inclination and reflectivity of the wane surface. The upper set of curves in FIG. 7 gives the ΔA signal values (solid line) and corresponding ΔB signal values (broken line) for a workpiece with a dull wane surface 12, while the lower curves give corresponding values for the same workpiece assuming it to have a more reflective wane surface. As pixels move onto the sawed flat top surface 11 of the workpiece, there will again be an abrupt rise in the ΔA (and ΔB) signal level, to a new and higher "plateau" level 84 that is maintained while the pixels wholly cover parts of the surface 11. The ΔA and ΔB signals will of course fall off rather quickly, to below the background level, as the scan passes onto a part of the workpiece that does not receive radiation or—as in the case of the side surface 13'—is outside the response field of the camera.

The relatively steep front wane surface 12 that is shown for the workpiece 6 in FIG. 7 is not illuminated by the rear radiation source 14', and therefore the ΔB signals change from measurement cycle to measurement cycle as indicated by the broken-line curves, not rising above the background level until the scan passes onto the sawed top surface 11, and thereafter abruptly rising to a higher level which is maintained until the scan passes onto the rear surface 13' of the workpiece. Although the surface 13' is illustrated as sawed and therefore highly reflective, it is at such an angle that the camera cannot receive radiation reflected from it; hence, as the scan passes that surface ΔB signal values decrease abruptly.

It will be seen that an edge of a workpiece itself (i.e., an outer edge) is denoted by a more or less steady but rapid change in ΔA signal from background level to a "plateau" value and in ΔB signal from a "plateau" value to background level. The exact location of an edge can be determined with good accuracy from the point at which the appropriate rising or falling signal succession has a value half of that at the "plateau" for the workpiece surface adjacent to that edge. Such location of an outside edge by the point of signal level that is "halfway up the hill" is valid both for a workpiece edge that is defined by a sawed surface (like the surface 13' in FIG. 7) and for one defined by an unfinished wane.

A different principle is applied for determining an inner workpiece edge (e.g., the edge between wane 12 and top surface 11 in FIG. 7) from the succession of ΔA and ΔB signals. For this, the local angle of inclination $\beta$ is computed for the ΔA, ΔB signal pair obtained during each measurement cycle, and the angle or its derivative is compared with a certain limit value. The inner edge is at the point where the angle $\beta$ or its derivative goes through that limit value and thereafter remains for a certain time at a value above that limit value.

As pointed out above, the parameters of a workpiece that is curved across its scanned surface, or across a substantial part of that surface, can be accurately defined in terms of the locations of the outer edges of the workpiece—determined as explained above—in combination with thickness data for the workpiece obtained from the ΔL signals and from a mechanical thickness gaging device, and local surface inclinations all across and along the workpiece calculated from the ΔA, ΔB signal pairs.

It will be evident that the length of each workpiece is readily ascertainable from the data obtained in scanning according to the principles of this invention.

Figure 11:
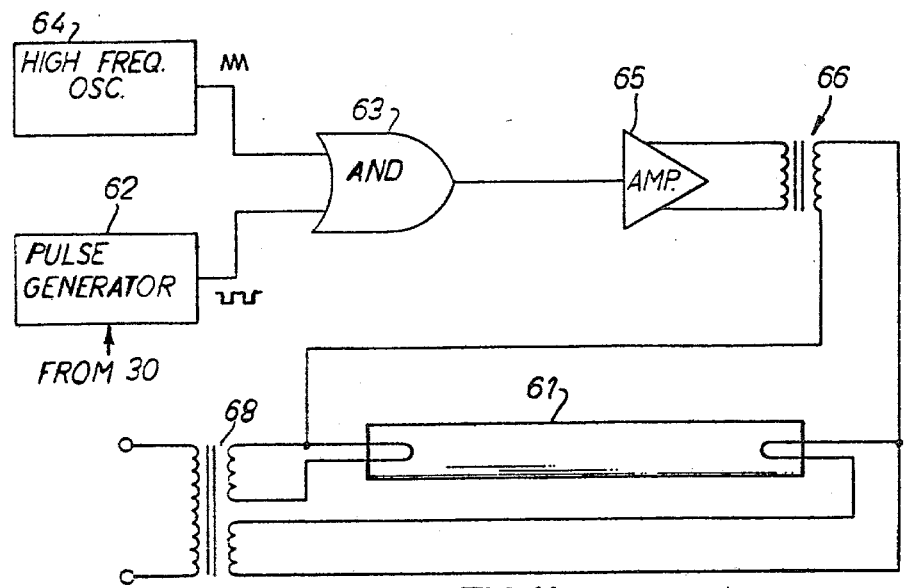
FIG. 11 is a circuit diagram of one form of apparatus for causing properly timed intermittent operation of a radiation source.

Turning now to an explanation of how the several detector elements are exposed to reflected radiation originating from the sources 14 and 14', respectively, at proper times in each measurement cycle, FIG. 11 illustrates one arrangement of apparatus whereby this can be accomplished.

Each of the radiation sources 14, 14' can comprise one or more gas discharge tubes 61. Under the control of the control instrumentality 30, a pulse generator 62 emits alternating ONE and ZERO square wave pulses at the frequency at which the discharge tube 61 is to be turned on and off. The pulse generator 62, which can be a Schmitt trigger, can have a pulse frequency on the order of 250 Hz. The output of the pulse generator 62 is fed to an AND-gate 63 that also receives an input from a high frequency oscillator 64 having a frequency on the order of 20 to 25 kHz. Through the AND-gate 63, the high frequency output of the oscillator 64 is passed to an amplifier 65 during the duration of each ONE pulse from the pulse generator 62. The amplifier 65, in turn, has its output connected to the primary of a step-up transformer 66. The voltage across the secondary of the transformer 66 is high enough for starting of the discharge tube 61, but the transformer 66 limits the current through the discharge tube 61 to a suitable value which, however, can be somewhat higher than would be drawn by the lamp when operating at its normal running voltage, owing to the short interval during which the current flows. With a discharge tube that needs filament current, such current is supplied from a filament transformer 68 that is coupled with the tube 61 in a suitable manner and is connected with a source of line voltage.

During the ZERO pulse of the pulse generator 62, the discharge in the tube 61 is of course extinguished, and its radiation quickly drops from the relatively high intensity required for producing an A or a B signal. However, owing to its fluorescence and any ambient lighting which may be present, radiation at the workpiece falls to the substantially lower intensity required for the R signal.

To provide for alternating illumination of the radiation sources 14, 14', the control instrumentality 30 causes the pulse generator 62 for each radiation source to issue a ONE signal at the same time that the pulse generator for the other source is issuing a ZERO signal. The frequency at which the radiation sources 14, 14' are alternately illuminated is so much higher than the 20 Hz image fusion frequency of the human eye that both light sources appear to be steadily illuminated, and there is no annoying flashing or flickering such as occurred with some prior scanning systems.

Figure 12:
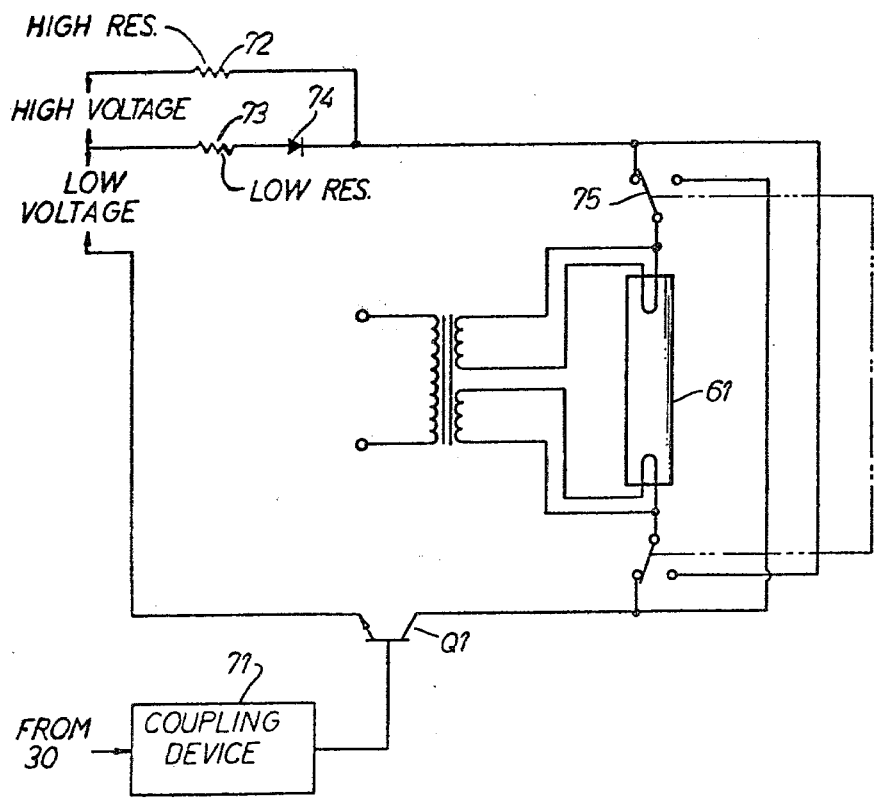
FIG. 12 illustrates a modified circuit for synchronized intermittent radiation source operation.

FIG. 12 shows a circuit that is suitable when higher radiation intensities are required, as when speeds of workpiece transport are such that the losses that arise from energizing a discharge tube with high frequency alternating current impose a practical limit upon the available power.

In the FIG. 12 arrangement each discharge tube 61 is energized with direct current. The base of transistor $Q_1$ is connected with the control device 30 through a suitable electronic coupling device 71 whereby the transistor is biased for conductivity at those times when the discharge tube 61 is to radiate. When conducting, transistor $Q_1$ connects the tube 61 with a source of high ignition voltage having high impedance current limiting means 72. Upon ignition, when the impedance of the discharge tube 61 abruptly diminishes, the tube draws running current from a low voltage source comprising a current limiting series resistor 73. A diode 74 in series with the resistor 73 prevents closure of the high voltage circuit by way of the resistor 73. A polarity reversing switch 75 provides for periodic reversal of the direction of current flow through the tube 61, for example with each successive measurement cycle, to prevent blackening of the tube.

The arrangement diagrammatically illustrated in FIG. 8 permits both of the radiation sources 14 and 14' to be steadily illuminated while nevertheless exposing each of the photoresponsive elements to pulses of reflected radiation from each of the radiation sources alternately, for production of pulsed A and B signals in the proper sequence. In this case, filters 81, 81' at the respective radiation sources 14, 14' cause radiation from the front source 14 to have a substantially different wavelength than radiation from the rear source 14'. Preferably, as shown in FIG. 10, the wavelengths of the radiation sources 14 and 14' not only differ substantially from one another but also differ from the monochromatic radiation from the lasers 27. At the lens or lens system of each of the array cameras 15 there is a rotating filter disc 82 that has four filter elements A', B', L' and R', each of which, in turn, comes into register with the optical system as the disc 82 rotates. The filter element A' passes only radiation of the wavelength propagated from the front radiation source 14, the filter element B' passes only radiation from the rear source 14', and the filter element L' passes only laser radiation. The filter element R' is opaque and thus provides a zero value R signal for normalizing the A, B and L signals with respect to amplifier drift and the like. The filter disc has a code line 84 for synchronizing exposure of the array. The code line is detected by an optical reading fork 86 which produces outputs that are fed to the control unit 30 to cause its pulse outputs to be issued at the proper times for control of the adder 35 and other synchronized units of the signal processing equipment 28. It will be apparent that the several detector elements will produce the same outputs as if the several radiation sources were pulsed, and consequently the signal processing equipment can be essentially the same as that described above.

Since cants and similar workpieces will normally pass through the measuring zone 7 with their narrower sawed surfaces 11 facing upward, the apparatus described to this point will take no measurements on the wider sawed bottom surfaces of such workpieces. However, it will be recognized that for a complete and definitive calculation of the geometry of the workpieces, they can be turned upside down after passing through the measuring zone 7 and either sent through the same measuring zone for a second scanning or allowed to continue through a second and similar measuring zone. Alternatively, the illustrated apparatus at the measuring zone 7 can be duplicated at the underside of that zone, with radiation sources under the measuring zone that cast radiation at upwardly oblique angles across the bottom surfaces of the workpiece, and with upwardly scanning array cameras.

It will also be apparent that the method of this invention lends itself to employment with workpieces that are maintained stationary in the measuring zone 7 while effective relative motion between each workpiece and the photoresponsive element array is produced by movement of the array cameras 15 or with the aid of a swinging mirror as disclosed in U.S. Pat. Nos. 3,886,372 and 3,963,938. Of course the remarkably high processing rates that can be attained with the present invention will not be fully realized if the workpieces are stationary during scanning, although all of the other advantages of the invention will be obtained.

From the foregoing description taken with the accompanying drawings it will be apparent that this invention provides an extremely fast and very accurate system for taking measurement information on elongated workpieces of irregular shape, which information can be fed to automatic data processing equipment for calculation of the profile or general configuration of the workpiece and of the trimming cuts that should be made to reduce the workpiece to a finished piece of optimum economic value.

I claim:

1. A method of obtaining information about surface configuration of a workpiece with the use of a photoresponsive detector element which has an optical axis, has a response field limited to small angles of divergence from its optical axis, and produces an output having a magnitude dependent upon the intensity of radiation that it detects in its response field, wherein said element is caused to scan across a workpiece in a direction substantially normal to its optical axis and while a pair of radiation sources that are spaced to opposite sides of said axis emit radiation towards the workpiece to be reflected from it for detection by the element, said method being characterized by:

during each of a succession of measurement cycles that are of uniform and substantially short duration, exposing said element to radiation which is reflected thereto from substantially one and the same small surface area on the workpiece but which originates alternately from each of said radiation sources substantially to the exclusion of radiation originating from the other.

2. A method of obtaining information about a workpiece with the use of an array comprising a plurality of adjacent photoresponsive detector elements that have respective optical axes which lie in a common plane, each of said elements having a response field limited to small angles of divergence from its optical axis and producing an output having a magnitude corresponding to the intensity of radiation that it detects in its response field, wherein said array is caused to scan across a workpiece in a direction substantially normal to said plane and at an ascertainable velocity while a pair of radiation sources that are spaced to opposite sides of said plane emit radiation towards the workpiece to be reflected from it for detection by elements of the array, said method being characterized by:

A. during the time that a workpiece is being scanned, issuing a cycle signal at each of a succession of regular time periods so that each pair of successive cycle signals defines a measurement cycle;

B. during each measurement cycle, exposing each detector element that has the workpiece within its response field to radiation originating from each in turn of said radiation sources, substantially to the exclusion of radiation originating from the other, the sequence of such exposures being the same for every measurement cycle and each such exposure occurring during a predetermined interval in the measurement cycle, to thus cause the detector element to produce a pair of discrete measurement outputs, one for each exposure; and C. so controlling the frequency of said cycle signals and the timing of said intervals in relation to the velocity of scan that
  (1) there is a substantial overlap between areas on the workpiece that are within the response field of a detector element during said intervals in each measurement cycle, which overlap defines a local area on the workpiece, and
  (2) the local areas for successive measurement cycles are in proximity to one another.

3. The method of claim 2, further characterized by:
D. during a further interval in each measurement cycle, exposing each detector element in the array to a reference level of radiation intensity that is substantially constant through successive measurement cycles and is substantially lower in intensity than detected radiation originating from said sources, to cause the detector element to issue a reference output for each measurement cycle; and E. subtracting the magnitude of the reference output for each measurement cycle from the magnitude of each of the measurement outputs for the same measurement cycle, to produce a pair of difference signals having respective magnitudes that are directly comparable with one another and with magnitudes of other difference signals.

4. The method of claim 2 wherein exposures are produced by energizing said radiation sources alternately.

5. The method of claim 4 wherein the alternate energization of said radiation sources occurs at a frequency substantially in excess of 20 Hz, so that both radiation sources appear to the eye to be operating steadily.

6. The method of claim 4 wherein the duration of a measurement cycle is on the order of four milliseconds.

7. The method of claim 2 wherein each said exposure is produced by:
  (1) causing each of said radiation sources to substantially steadily emit radiation of a wavelength substantially different from that emitted by the other, and
  (2) alternately passing in front of the detector element filters that respectively block radiation of one and the other of said wavelengths.

8. The method of claim 2, further characterized by:
D. during a further interval in each measurement cycle causing a narrow beam of radiation to be emitted substantially in said plane and at an oblique angle to a surface of the workpiece that is within the response fields of the array, so that reflection of said beam from said surface produces a spot of radiation which is detected by one of said detector elements and causes that element to produce a thickness signal, the particular element producing that signal being dependent upon a function of thickness of the workpiece.

9. The method of claim 8 wherein the response field of each detector element is so narrow that said spot of radiation can be detected by a set of adjacent detector elements, each of which issues a thickness output, further characterized by:
  (1) generating a threshold output having a predetermined magnitude,
  (2) comparing the magnitude of each of the thickness outputs issued by the detector elements of said set during a measurement cycle with said threshold output,
  (3) discarding all of said thickness outputs that have magnitudes lower than that of said threshold output.

10. The method of claim 2 wherein said array is stationary and the workpiece is moved to effect scanning, further characterized by:
D. issuing a position pulse signal each time the workpiece advances through a predetermined distance, so that said difference signals for each measurement cycle can be correlated to the position of the workpiece relative to said plane during the measurement cycle.

11. A method of obtaining information about variations in thickness of a workpiece as measured between substantially opposite surfaces thereon and in one direction along one of said surfaces by scanning said one surface in said direction by means of an array comprising a plurality of adjacent photoresponsive detector elements that have respective optical axes which lie in a common plane that is substantially normal to said direction, each of said elements having a response field limited to small angles of divergence from its optical axis and producing an output in response to radiation that it detects in its response field, said method being characterized by:

A. during scanning, issuing a position pulse each time the scan advances through a predetermined distance; and B. causing a narrow beam of radiation to be emitted in a direction such that the beam
  (1) is substantially contained in said plane and
  (2) is at an oblique angle to said surface, so that the beam is reflected from said surface as a small spot of radiation that is detected by one of said detector elements, the particular detector element which, during any interval between position pulses, produces an output in response to such detection being a function of the local thickness of the workpiece at the location of the scan during that interval.

12. The method of claim 11 wherein the response field of each detector element is so narrow that said spot of radiation can be detected by a plurality of adjacent detector elements, further characterized by:
C. for each interval between position pulses, comparing the magnitude of the output produced by each of said plurality of detector elements with a threshold level magnitude;
D. discarding all of said outputs that have magnitudes less than said threshold level magnitude; and
E. from the remainder of said outputs calculating the center of said spot of radiation.

13. A method of obtaining information about a workpiece with the use of an array comprising a plurality of adjacent photoresponsive detector elements that have respective optical axes which lie in a common plane, each of said elements having a response field limited to small angles of divergence from its optical axis and producing an output having a magnitude corresponding to the intensity of radiation that it detects in its response field, wherein said array is caused to scan a workpiece in a direction substantially normal to said plane and at an ascertainable velocity while a pair of radiation sources that are spaced to opposite sides of said plane emit radiation towards the workpiece to be reflected from it for detection by elements of the array, said method being characterized by:
A. during the time that a workpiece is being scanned, issuing a cycle timing signal at each of a succession of regular measurement cycle periods which are of such short duration that a local area on the workpiece is within the response field of a detector element during the whole of a measurement cycle period;
B. during each measurement cycle period exposing each detector element that has the workpiece within its response field successively to
(1) radiation originating from one of said radiation sources substantially to the exclusion of radiation originating from the other, to cause the element to issue a first measurement output having a magnitude dependent upon the intensity of reflected radiation from said one source,
(2) radiation originating from said other radiation source substantially to the exclusion of radiation originating from said one source, to cause the element to issue a second measurement output having a magnitude depending upon the intensity of reflected radiation from said other source, and
(3) a substantially lower level of radiation than that which gives rise to issuance of said measurement outputs, to cause the element to issue a reference output having a substantially low magnitude; and
C. for each of at least certain of said detector elements, subtracting the magnitude of the reference output issued by the element during each measurement cycle period from the magnitude of each of its first and second measurement outputs issued during the same measurement cycle period, to produce first and second difference values, respectively, that are directly comparable with one another and with difference values that originate from others of said certain detector elements.

14. Apparatus for obtaining information about a workpiece at a measuring zone, said apparatus being of the type comprising a photoresponsive detector element that has an optical axis extending through said measuring zone and has a response field limited to small angles of divergence from said optical axis, said element being adapted to produce an output that has a magnitude corresponding to the intensity of radiation that it detects in its response field, and a pair of radiation sources that are spaced in opposite directions from said axis, said radiation sources being arranged to emit radiation towards said measuring zone for reflection from a workpiece in said zone to the element, said apparatus being characterized by:
A. means for exposing the detector element, successively and briefly, during each of a regular succession of cycles,
(1) to a level of radiation substantially lower than that originating from said sources, to cause the element to produce an R output, and
(2) to radiation reflected from a workpiece and originating from each of said radiation sources substantially to the exclusion of the other, to cause the element to produce an A output and a B output;
B. comparison means connected with said detector element and comprising a short term memory;
C. means for transferring each in turn of the A, B and R outputs obtained during a cycle to said comparison device, for subtraction from said A and B outputs of the R output for the cycle, to produce ΔA and ΔB difference signals, respectively, for the cycle; and
D. means for so controlling relative movement between a workpiece at the measuring zone and said detector element that the A and B signals for a cycle are produced in response to reflections from surface areas of the workpiece that substantially overlap one another in a local area, so that the inclination of the local area on the workpiece can be determined from the ΔA and ΔB signals for that local area.

15. The apparatus of claim 14 wherein said detector element comprises one of an array of detector elements of an array camera which have their respective optical axes lying in a common plane that is normal to said direction, further characterized by:
G. a laser arranged to have its beam in said plane and extending obliquely to said axes for localized reflection of its radiation from a workpiece in said zone; and
H. means for pulsingly energizing the laser at a time during each cycle when neither an A nor a B nor an R output is being produced, so that an L output is produced by at least one of the detector elements of said array in response to reflected laser radiation, the particular element that produces said L output being dependent upon local thickness of the workpiece.

16. A method of obtaining information about surface configuration of a workpiece with the use of a photoresponsive detector element which has an optical axis, has a response field limited to small angles of divergence from its optical axis, and produces an output having a magnitude dependent upon the intensity of radiation that it detects in its response field, wherein a pair of radiation sources that are spaced to opposite sides of said axis emit radiation towards the workpiece to be reflected from it for detection by the element, said method being characterized by:

A. during a measurement cycle that is of short duration, exposing said element to radiation which is reflected thereto from substantially one and the same small surface area on the workpiece but which originates alternately from each of said radiation sources substantially to the exclusion of radiation originating from the other; and B. taking from said element the outputs that result from each of such exposures to radiation originating from the respective radiation sources.

17. A method of obtaining information about a workpiece with the use of an array comprising a plurality of adjacent photoresponsive detector elements that have respective optical axes which lie in a common plane, each of said elements having a response field limited to small angles of divergence from its optical axis and producing an output having a magnitude corresponding to the intensity of radiation that it detects in its response field, wherein a pair of radiation sources that are spaced to opposite sides of said plane emit radiation towards the workpiece to be reflected from it for detection by elements of the array, said method being characterized by:

A. exposing each detector element that has the workpiece within its response field to radiation originating from each in turn of said radiation sources, substantially to the exclusion of radiation originating from the other, each such exposure occurring during a predetermined interval, to thus cause the detector element to produce a pair of discrete measurement outputs, one for each exposure; and B. so controlling the timing of said intervals relative to the movement of the workpiece through said intervals that there is a substantial overlap between areas on the workpiece that are within the response field of a detector element during said intervals, which overlap defines a local area on the workpiece.

18. A method of obtaining information about the geometry of a workpiece by scanning it with an array comprising a plurality of photoresponsive detector elements that have respective optical axes, each of said detector elements having a response field limited to small angles of divergence from its optical axis and producing an output in response to radiation that it detects in its response field, the response fields of the detector elements being arranged in a substantially regular pattern, the workpiece being so disposed during scanning that it has a substantially large surface facing towards said array and intersected by said optical axes, and the workpiece being illuminated for scanning by radiation from a pair of radiation sources which are spaced in substantially opposite directions from the workpiece and the array and which emit radiation towards said surface at opposite angles that are substantially oblique both to said surface and to said optical axes, said method being characterized by:

so controlling
(1) relative movement between said array and the workpiece and
(2) the time during which each detector element that has the workpiece in its field of view is exposed to radiation orginating from each of said radiation sources and reflected from the workpiece, that each such detector element is, during a brief time interval, exposed to radiation which is reflected to it from substantially one and the same small surface area on the workpiece but which originates first from one and then from the other of said two radiation sources.

19. The method of claim 18, further characterized by: during said brief time interval further causing each such detector element to be exposed to a reference level of radiation substantially corresponding to extinction of radiation at both of said radiation sources.

20. Apparatus for obtaining information about surface configuration of a workpiece, said apparatus being of the type comprising a photoresponsive detector element which has an optical axis and which produces an output having a magnitude dependent upon the intensity of radiation that it detects within a response field limited to small angles of divergence from said optical axis, means for causing said detector element to scan at an ascertainable velocity in a direction substantially normal to its optical axis across a workpiece that extends across its response field, and a pair of radiation sources that are spaced to opposite sides of said optical axis and each of which emits radiation in a direction away from said detector element and obliquely across said axis for reflection from a workpiece to said element, said apparatus being characterized by:

A. means for defining a succession of measurement cycle time intervals that are of a uniform and substantially short duration which is so related to the velocity of scan that there is a substantial overlap between the respective local areas of a workpiece surface which are within said response field at the beginning and at the end of each measurement cycle time interval; and B. means for restricting exposure of said detector element to radiation which, during every radiation cycle, originates alternately from each of said radiation sources substantially to the exclusion of radiation originating from the other and which is reflected from a workpiece.

* * * * *